US012584088B2

(12) United States Patent
Johnson et al.

(10) Patent No.: US 12,584,088 B2
(45) Date of Patent: Mar. 24, 2026

(54) HIGHLY DURABLE PERMEABLE FLUOROPOLYMER CELL CULTURE BAG

(71) Applicant: W. L. Gore & Associates, Inc., Newark, DE (US)

(72) Inventors: Matthew A. Johnson, Newark, DE (US); Susie R. Enache, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 1009 days.

(21) Appl. No.: 17/605,313

(22) PCT Filed: Apr. 24, 2020

(86) PCT No.: PCT/US2020/029753
§ 371 (c)(1),
(2) Date: Oct. 21, 2021

(87) PCT Pub. No.: WO2020/219834
PCT Pub. Date: Oct. 29, 2020

(65) Prior Publication Data
US 2022/0186165 A1     Jun. 16, 2022

Related U.S. Application Data

(60) Provisional application No. 62/838,127, filed on Apr. 24, 2019.

(51) Int. Cl.
*C12M 1/00*          (2006.01)
*C12M 1/04*          (2006.01)
*C12M 3/00*          (2006.01)
(52) U.S. Cl.
CPC ............ *C12M 23/24* (2013.01); *C12M 23/14* (2013.01); *C12M 23/22* (2013.01); *C12M 23/28* (2013.01); *C12M 23/44* (2013.01)

(58) Field of Classification Search
None
See application file for complete search history.

(56) References Cited

U.S. PATENT DOCUMENTS 7,521,010 B2     4/2009   Kennedy
9,926,524 B2     3/2018   Clark
                 (Continued)

FOREIGN PATENT DOCUMENTS

JP          2017524575 A     8/2017

OTHER PUBLICATIONS

International Search Report and Written Opinion from International Application No. PCT/US2020/029753 dated Jun. 15, 2020.
                 (Continued)

*Primary Examiner* — Ramsey Zacharia
(74) *Attorney, Agent, or Firm* — Faegre Drinker Biddle & Reath LLP

(57)          ABSTRACT

A cell culture bag includes a body formed of a composite film including a first fluoropolymer and a second fluoropolymer. The body defines a cell culture compartment configured to hold a cell culture. The first fluoropolymer has a first thickness and the second fluoropolymer at least partially impregnates the first thickness of the first fluoropolymer. The composite film has a second thickness from 0.01 mm to 0.059 mm and a tensile strength in one direction of 10,000 psi to 92,000 psi. The composite film also has $O_2$ flux of 2,000 $cm^3/m^2$/atm/day to 20,000 $cm^3/m^2$/atm/day and a total transmittance from 70% to 100%. A cell culture assembly includes a plurality of the cell culture bags connected in series. A cell culture container includes a cell culture compartment and a composite film connected to the cell culture compartment, the composite film including a first fluoropolymer and a second fluoropolymer.

20 Claims, 3 Drawing Sheets

(56) References Cited

U.S. PATENT DOCUMENTS

| | | |
|---|---|---|
| 2005/0238872 A1 | 10/2005 | Kennedy et al. |
| 2015/0344844 A1 | 12/2015 | Better |
| 2016/0177245 A1 | 6/2016 | Johnson et al. |
| 2016/0177246 A1 | 6/2016 | Lundgren et al. |
| 2016/0177247 A1 | 6/2016 | Clark et al. |
| 2018/0312793 A1 | 11/2018 | Clark |
| 2019/0032011 A1 | 1/2019 | Better |

OTHER PUBLICATIONS

Wargenau et al., "Protein film formation on cell culture surfaces investigated by quartz crystal microbalance with dissipation monitoring and atomic force microscopy," Colloids and Surfaces, B: Biointerfaces (2019); 183—pp. 1-8.

200

214

216

202

HIGHLY DURABLE PERMEABLE FLUOROPOLYMER CELL CULTURE BAG

FIELD

The present disclosure relates generally to gas permeable materials or components, and more specifically, to a fluoropolymer cell culture bag that has non-polar gas permeation.

BACKGROUND

Cell and gene therapies are increasingly viable methods for treating many conditions including various cancers, neurological diseases, infectious diseases such as tuberculosis and cystic fibrosis, ulcerative colitis, peripheral artery disease, aneurysm, heart disease, Alzheimer's and Parkinson's diseases, autism, ophthalmology conditions, diabetes, and other pathologies. With respect to cell and gene therapies in general, a variety of cell types may be grown in vitro. In vitro cell culturing is a complex process by which cells are grown under controlled conditions, outside of their natural environment, but as close to their natural in vivo conditions as possible.

One method for culturing cells in vitro is through the use of cell culture bags, such fluoropolymer cell culture bags, which reduce the risk of contamination for the cell culture because the cell culture bags are disposable and provide a closed system. However, some current fluoropolymer cell culture bags lack the durability to robustly serve as cell culture bags. Specifically, current fluoropolymer cell culture bags have a tensile strength that may cause them to break during handling. Durability of these cell culture bags can be increased by increasing the thickness of the fluoropolymer film used to form the cell culture bag. Increasing the film thickness, however, can result in a reduction in the gas permeation of gases such as oxygen ($O_2$) and carbon dioxide ($CO_2$), both of which are needed for the cultured cells to survive. Thus, there is need for a cell culture bag that can withstand the stresses of handling while providing an environment suitable for cellar metabolism and growth.

Another existing method for culturing cells in vitro is to use a cell culture container such as a flask that contains a fluoropolymer film permeable to gases such as $O_2$ and $CO_2$. Current cell culture containers also include fluoropolymer composite films that have tensile strengths that may cause them to break during handling. Additionally, current cell culture containers may include "dirty" films, e.g., a composite film that contains an undesirable amount of extractables and/or leachables. Further, conventional fluoropolymer composite films do not have the clarity required to see into the cell culture container. Thus, there is a need for a cell culture container that can withstand the stresses of handling while enabling visibility into the container and providing an environment suitable for cellular metabolism and growth.

SUMMARY

The summary is a high-level overview of various aspects of the invention and introduces some of the concepts that are further detailed in the Detailed Description section below. This summary is not intended to identify key or essential features of the claimed subject matter, nor is it intended to be used in isolation to determine the scope of the claimed subject matter. The subject matter should be understood by reference to the appropriate portions of the entire specification, any or all drawings, and each claim.

Embodiments of the present disclosure relate to cell culture bags including, but not limited to, a body formed of a composite film including a first fluoropolymer and a second fluoropolymer, the body defining a cell culture compartment configured to hold a cell culture. The first fluoropolymer has a first thickness and the second fluoropolymer at least partially impregnates the first thickness of the first fluoropolymer. The composite film has a second total thickness from 0.01 mm to 0.059 mm, where the second total thickness is the combined thickness of the first and second fluoropolymers. The composite film has a tensile strength in one direction from 10,000 psi to 92,000 psi. The composite film has an $O_2$ flux from 2,000 $cm^3/m^2$/atm/day to 20,000 $cm^3/m^2$/atm/day and a total transmittance from 70% to 100%.

In some embodiments, the composite film does not comprise silicone.

In some embodiments, the second fluoropolymer impregnates from 0.00001 mm to 0.02 mm of the first thickness of the first fluoropolymer.

In some embodiments, the composite film has a total thickness from 0.02 mm to 0.059 mm.

In some embodiments, the composite film has a total organic carbon (TOC) in water of 0.00001 $mg/cm^2$ to 1 $mg/cm^2$.

In some embodiments, the composite film has an $O_2$ flux from 8,000 $cm^3/m^2$/atm/day to 15,000 $cm^3/m^2$/atm/day.

In some embodiments, the composite film has a tensile strength in at least one direction from 20,000 psi to 92,000 psi.

In some embodiments, a peel strength of the composite film is 0.25 N/mm to 10 N/mm.

In some embodiments, the first fluoropolymer is expanded polytetrafluoroethylene and the second fluoropolymer is fluorinated ethylene propylene.

Embodiments of the present disclosure relate to cell culture bags including, but not limited to, a tube extending from a first end to a second end and defining a cell culture compartment. The tube is formed of a first composite film including a first fluoropolymer and a second fluoropolymer. The first fluoropolymer has a first thickness and the second fluoropolymer at least partially impregnates the first thickness of the first fluoropolymer. The first composite film has a second thickness of 0.01 mm to 0.059 mm. The first composite film has an $O_2$ flux of 2,000 $cm^3/m^2$/atm/day to 20,000 $cm^3/m^2$/atm/day. The first composite film has a tensile strength of 10,000 psi to 92,000 psi. The first composite film has a total transmittance of at least 70%. The cell culture bags also include first joint at a first end, a second composite film configured to be folded over the first joint to form a first lap seam over the first joint, and a second lap seam extending longitudinally from the first end to the second end, the second lap seam being formed by overlapping edges of the first composite film.

In some embodiments, the cell culture bags further include a second joint at a second end and a third composite film configured to be folded over the second joint to form a third lap seam.

In some embodiments, the second fluoropolymer impregnates 0.00001 mm to 0.005 mm of the first thickness of the first fluoropolymer.

In some embodiments, the first composite film has a thickness of 0.02 mm to 0.059 mm.

In some embodiments, the first composite film a total organic carbon (TOC) of less than 1 $mg/cm^2$.

In some embodiments, the first composite film has an $O_2$ flux from 8,000 $cm^3/m^2$/atm/day to 15,000 $cm^3/m^2$/atm/day.

In some embodiments, the first composite film has a tensile strength in at least one direction from 20,000 psi to 92,000 psi.

In some embodiments, the first fluoropolymer is expanded polytetrafluoroethylene and the second fluoropolymer is fluorinated ethylene propylene.

In some embodiments, the first fluoropolymer is densified expanded polytetrafluoroethylene and the second fluoropolymer is fluorinated ethylene-propylene.

In some embodiments, the cell culture bags further include at least one access port in fluid communication with the cell culture compartment.

In some embodiments, the cell culture comprises at least one of connective tissue cells, skeletal cells, cardiac cells, epithelial cells, neural cells, endocrine cells, immune cells, lymphocytes, melanocytes, tumor cells, or combinations thereof.

In some embodiments, the first and second composite films are the same.

In some embodiments, the third composite film is the same as at least one of the first or the second composite films.

In some embodiments, a peel strength of the first composite film is 0.25 N/mm to 10 N/mm.

Embodiments of the present disclosure also relate to cell culture assemblies including, but not limited to, a plurality of cell culture bags connected in series. Each of the cell culture bags includes a body formed of a composite film including a first fluoropolymer and a second fluoropolymer, the body defining a cell culture compartment configured to hold a cell culture. The first fluoropolymer has a first thickness and the second fluoropolymer at least partially impregnates the first thickness of the first fluoropolymer. The composite film has a second thickness from 0.01 mm to 0.059 mm. The composite film has a tensile strength in one direction from 10,000 psi to 92,000 psi. The composite film has an $O_2$ flux from 2,000 $cm^3/m^2/atm/day$ to 20,000 $cm^3/m^2/atm/day$ and a total transmittance of the composite film is from 70% to 100%.

In some embodiments, a first cell culture bag of the plurality of cell culture bags has a first $O_2$ flux and a second cell culture bag of the plurality of cell culture bags has a second $O_2$ flux.

In some embodiments, the first $O_2$ flux and the second $O_2$ flux are different.

In some embodiments, a first cell culture bag of the plurality of cell culture bags has a first volume and a second cell culture bag of the plurality of cell culture bags has a second volume.

In some embodiments, the first volume is different than the second volume.

In some embodiments, a first cell culture bag of the plurality of cell culture bags is configured for at least one of cell transfection or cell activation.

In some embodiments, a second cell culture bag of the plurality of cell culture bags is configured for cell expansion.

Embodiments of the present disclosure also relate to cell culture containers including a cell culture compartment configured to receive a cell culture. The cell culture containers also include a composite film connected to the cell culture compartment, the composite film including a first fluoropolymer and a second fluoropolymer. The first fluoropolymer has a first thickness and the second fluoropolymer at least partially impregnates the first thickness of the first fluoropolymer. The composite film has a second thickness from 0.01 mm to 0.059 mm. The composite film has a tensile strength in one direction from 10,000 psi to 92,000 psi. The composite film has an $O_2$ flux from 2,000 $cm^3/m^2/atm/day$ to 20,000 $cm^3/m^2/atm/day$ and a total transmittance of the composite film is from 70% to 100%.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the present disclosure.

DETAILED DESCRIPTION

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

Described herein are cell culture bags and containers that include a composite film for in vitro cultivation of cells. Also described herein are methods for forming the composite film used to form the cell culture bags and containers. In some embodiments, the composite film has an $O_2$ flux that promotes cellular metabolism and growth within the cell culture container. In addition, in some embodiments, the composite film also has a tensile strength sufficient to reduce or even prevent tearing or leaking of the cell culture bag or container during handling. In some embodiments, the composite film is densified. The cell culture bags and containers described herein may be useful for processing cells from patients having a pathological disease or condition where loss of cells within the cell culture or insufficient growth of the cultured cells can impact the success of the treatment.

Figure 1:
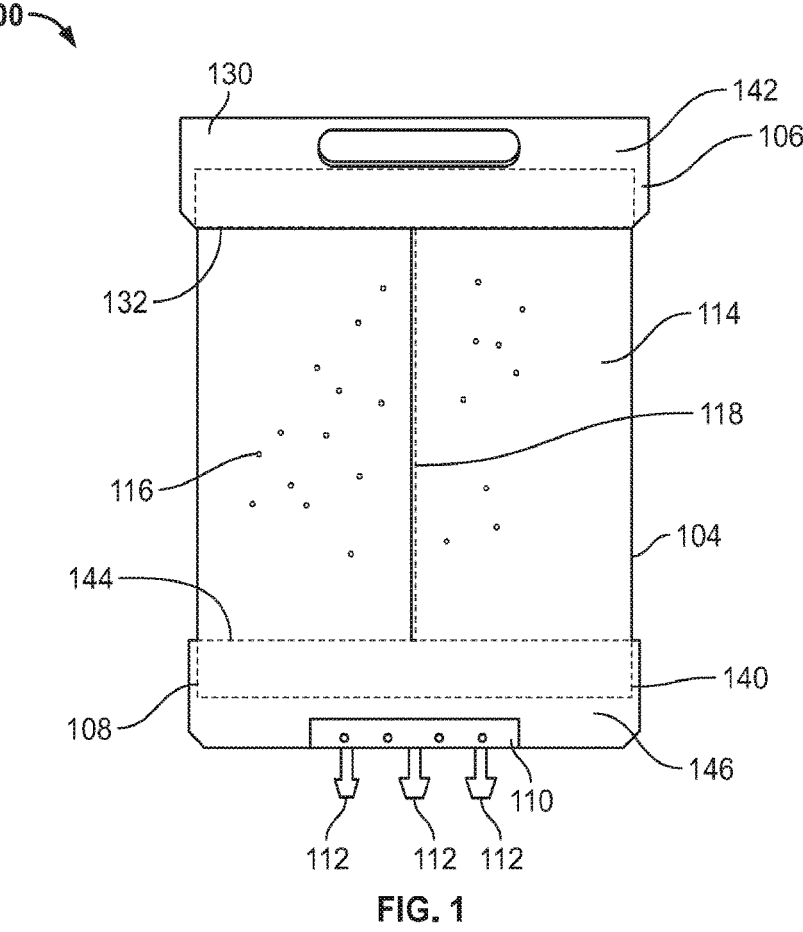
FIG. 1 is a top view of a cell culture bag in accordance with some embodiments herein.
Figure 2:
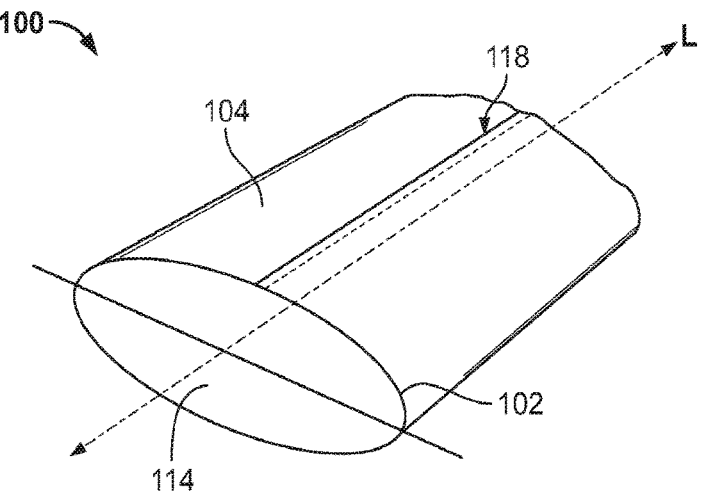
FIG. 2 is a perspective view of a composite film tube of a cell culture bag in accordance with some embodiments herein.

FIGS. 1 and 2 each depict a cell culture bag 100, according to some embodiments of the present disclosure. The cell culture bag 100 is formed of a composite film tube 104 which defines a cell culture compartment 114 therein, a first end 106, and a second end 108. The first end 106 is a handle end while the second end 108 is a port end. In one embodiment, the second end 108 has a port adapter 110 and at least one sealable port 112 in fluid communication with the cell culture compartment 114 for insertion, removal, sampling and feeding of a cell culture 116 therein.

The composite film tube 104 is formed from at least one composite film 102. A "composite film" is defined herein as a film formed of at least two different materials or films. For example, in some embodiments, the composite film 102 may be formed by layering at least two materials or films and applying heat and/or pressure so as to result in the layers of the resultant composite film 102 not being removable from each other.

In one embodiment, the composite film 102 is densified generally in accordance with the teachings provided in U.S. Pat. No. 7,521,010 to Kennedy et al., which is incorporated by reference herein.

In some embodiments, the composite film 102 contains a non-polar gas permeable fluoropolymer composite film. In some embodiments, the cell culture bag 100 includes a gas permeable fluoropolymer composite film because fluoropolymer composite films are biologically, chemically and immunologically compatible with the cell culture.

In some embodiments, the composite film 102 of the cell culture bag 100 may include, but is not limited to, the following materials: fluorinated ethylene-propylene (FEP), tetrafluoroethylene (TFE), modified polytetrafluoroethylene, perfluoroalkoxy (PFA), polyvinyl fluoride (PVF), polychlorotrifluoroethylene (PCTFE), polyethylenetetrafluroethylene (ETFE), chlorotrifluoroethlyenevinylidene fluoride (FPM/FKM), polyethylenechlorotrifluoroethylene (ECTFE), perfluoroelastomer (FFPM/FFLM), perfluoropolyether (PFPE), tetrafluoroethylene and perfluoromethyl vinylether copolymer (MFA), chlorotrifluoroethylenevinylidene fluoride copolymer (FTFE/VDF), and any combination thereof.

Expanded polytetrafluoroethylene (ePTFE) is referred to herein for ease of discussion, but it is to be appreciated that expanded modified polytetrafluoroethylene (PTFE), expanded blends of PTFE, expanded copolymers of PTFE, and PTFE homopolymers are all considered to be within the purview of the invention. Patents have been issued on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. Pat. No. 8,647,144 to Ford; and U.S. Pat. No. 9,139,669 to Xu et al.

In some embodiments, a material for the composite film 102 includes expanded polytetrafluoroethylene (ePTFE).

In some embodiments, a material for the composite film 102 includes densified expanded polytetrafluoroethylene (ePTFE).

In some embodiments, the film(s) and/or material(s) for the composite film 102 does not include silicone.

In some embodiments, the composite film 102 includes a first material and a second material. In some embodiments, each of the first material and the second material is a fluoropolymer. In some embodiments, the first material is ePTFE and the second material is FEP. In some embodiments, the composite film 102 is made generally in accordance with the teachings provided in U.S. Pat. No. 7,521,010 to Kennedy, et al., which is incorporated by reference herein.

In some embodiments, the first material is at least partially impregnated with the second material to form a highly durable mechanical bond. Specifically, in some embodiments, the second material extends at least partially into a thickness of the first material. In some embodiments, the second material impregnates from 0.00001 mm to 0.02 mm into the first material. In other embodiments, the second material impregnates from 0.00005 mm to 0.02 mm into the first material. In other embodiments, the second material impregnates from 0.0001 mm to 0.02 mm into the first material. In other embodiments, the second material impregnates from 0.0005 mm to 0.02 mm into the first material. In other embodiments, the second material impregnates from 0.001 mm to 0.02 mm into the first material. In other embodiments, the second material impregnates from 0.005 mm to 0.02 mm into the first material. In other embodiments, the second material impregnates from 0.01 mm to 0.02 mm into the first material.

In some embodiments, the second material impregnates from 0.00001 mm to 0.01 mm into the first material. In other embodiments, the second material impregnates from 0.00001 mm to 0.005 mm into the first material. In other embodiments, the second material impregnates from 0.00001 mm to 0.001 mm into the first material. In other embodiments, the second material impregnates from 0.00001 mm to 0.0005 mm into the first material. In other embodiments, the second material impregnates from 0.00001 mm to 0.0001 mm into the first material. In other embodiments, the second material impregnates from 0.00001 mm to 0.00005 mm into the first material.

In some embodiments, the second material impregnates from 0.0001 mm to 0.005 mm into the first material. In other embodiments, the second material impregnates from 0.0005 mm to 0.001 mm into the first material. In other embodiments, the second material impregnates from 0.00005 mm to 0.005 mm into the first material. In other embodiments, the second material impregnates from 0.001 mm to 0.005 mm into the first material. In other embodiments, the second material impregnates from 0.005 mm to 0.01 mm into the first material.

In some embodiments, the composite film 102 includes a first material that is impregnated with the second material on both a first side and a second side of the first material.

In some embodiments, the composite film 102 includes a first material that is impregnated with a second material on one side (e.g., first side) of the first material and is impregnated with a third material on an opposing side (e.g., second side) of the first material.

A characteristic of the composite film 102 for nurturing a cell culture is Total Organic Carbon (TOC) in water. As defined herein, TOC is the amount of carbon bound in an organic compound and is often used as a non-specific indicator of water quality or cleanliness of pharmaceutical equipment, among other things. TOC is utilized as a process control attribute in the biotechnology industry to monitor the performance of unit operations that employ purification and distribution systems.

In some embodiments, the composite film 102 has a TOC of less than 0.0005 mg/cm$^2$. In other embodiments, the composite film has a TOC from 0.00001 mg/cm$^2$ to 1 mg/cm$^2$. In other embodiments, the composite film 102 has a TOC from 0.00005 mg/cm$^2$ to 1 mg/cm$^2$. In other embodiments, the composite film 102 has a TOC from 0.0001 mg/cm$^2$ to 1 mg/cm$^2$. In other embodiments, the composite film 102 has a TOC from 0.005 mg/cm$^2$ to 1 mg/cm$^2$. In other embodiments, the composite film 102 has a TOC from 0.01 mg/cm$^2$ to 1 mg/cm$^2$. In other embodiments, the composite film 102 has a TOC from 0.1 mg/cm$^2$ to 1 mg/cm$^2$. In other embodiments, the composite film 102 has a TOC from 0.5 mg/cm$^2$ to 1 mg/cm$^2$.

In some embodiments, the composite film 102 has a TOC from 0.00001 mg/cm$^2$ to 0.5 mg/cm$^2$. In other embodiments, the composite film 102 has a TOC from 0.00001 mg/cm$^2$ to 0.1 mg/cm$^2$. In other embodiments, the composite film 102 has a TOC from 0.00001 mg/cm$^2$ to 0.05 mg/cm$^2$. In other embodiments, the composite film 102 has a TOC from 0.00001 mg/cm$^2$ to 0.01 mg/cm$^2$. In other embodiments, the composite film 102 has a TOC from 0.00001 mg/cm$^2$ to 0.005 mg/cm$^2$. In other embodiments, the composite film 102 has a TOC from 0.00001 mg/cm$^2$ to 0.001 mg/cm$^2$. In other embodiments, the composite film 102 has a TOC from 0.00001 mg/cm$^2$ to 0.0005 mg/cm$^2$.

In some embodiments, the composite film 102 has a TOC from 0.00005 mg/cm$^2$ to 0.005 mg/cm$^2$. In some embodiments, the composite film 102 has a TOC from 0.0008 mg/cm$^2$ to 0.02 mg/cm$^2$. In some embodiments, the composite film 102 has a TOC from 0.006 mg/cm$^2$ to 0.4 mg/cm$^2$. In some embodiments, the composite film 102 has a TOC from 0.04 mg/cm$^2$ to 0.8 mg/cm$^2$. In some embodiments, the composite film 102 has a TOC from 0.5 mg/cm$^2$ to 0.75 mg/cm$^2$. In some embodiments, the composite film 102 has a TOC from 0.00005 to O. 0001 mg/cm$^2$.

In some embodiments, the composite film 102 has a tensile strength of 10,000 psi (69 MPa) or greater in at least one direction. In another embodiment, the tensile strength of the composite film 102 in at least one direction is 12,000 psi or greater. In another embodiment, the tensile strength of the composite film 102 in at least one direction is 15,000 psi or greater. In another embodiment, the tensile strength of the composite film 102 in at least one direction is 17,500 psi or greater. In another embodiment, the tensile strength of the composite film 102 is 20,000 psi or greater in at least one direction. In another embodiment, the tensile strength of the composite film 102 in at least one direction is 35,000 psi or greater. In another embodiment, the tensile strength of the composite film 102 is 50,000 psi or greater in at least one direction. In another embodiment, the tensile strength of the composite film 102 in at least one direction is 60,000 psi or greater. In another embodiment, the tensile strength of the composite film 102 is 75,000 psi or greater in at least one direction. In another embodiment, the tensile strength of the composite film 102 is 80,000 psi or greater in at least one direction. In another embodiment, the tensile strength of the composite film 102 is less than or equal to 92,000 psi in at least one direction.

In some embodiments, the composite film 102 has a tensile strength in at least one direction from 10,000 psi to 92,000 psi. In other embodiments, the composite film 102 has a tensile strength in at least one direction from 10,000 psi to 80,000 psi. In other embodiments, the composite film 102 has a tensile strength in at least one direction from 10,000 psi to 60,000 psi. In other embodiments, the composite film 102 has a tensile strength in at least one direction from 10,000 psi to 50,000 psi. In other embodiments, the composite film 102 has a tensile strength in at least one direction from 10,000 psi to 25,000 psi. In other embodiments, the composite film 102 has a tensile strength in at least one direction from 10,000 psi to 20,000 psi. In other embodiments, the composite film 102 has a tensile strength in at least one direction from 10,000 psi to 15,000 psi. In other embodiments, the composite film 102 has a tensile strength in at least one direction from 10,000 psi to 12,000 psi.

In some embodiments, the composite film 102 has a tensile strength in at least one direction from 12,000 psi to 92,000 psi. In other embodiments, the composite film 102 has a tensile strength in at least one direction from 15,000 psi to 92,000 psi. In other embodiments, the composite film 102 has a tensile strength in at least one direction from 20,000 psi to 92,000 psi. In other embodiments, the composite film 102 has a tensile strength in at least one direction from 25,000 psi to 92,000 psi. In other embodiments, the composite film 102 has a tensile strength in at least one direction from 40,000 psi to 92,000 psi. In other embodiments, the composite film 102 has a tensile strength in at least one direction from 50,000 psi to 92,000 psi. In other embodiments, the composite film 102 has a tensile strength in at least one direction from 75,000 psi to 92,000 psi.

In some embodiments, the composite film 102 has a tensile strength in at least one direction from 12,000 psi to 75,000 psi. In other embodiments, the composite film 102 has a tensile strength in at least one direction from 25,000 psi to 60,000 psi. In other embodiments, the composite film 102 has a tensile strength in at least one direction from 15,000 psi to 45,000 psi. In other embodiments, the composite film 102 has a tensile strength in at least one direction from 50,000 psi to 80,000 psi. In other embodiments, the composite film 102 has a tensile strength in at least one direction from 45,000 psi to 65,000 psi. In other embodiments, the composite film 102 has a tensile strength in at least one direction from 60,000 psi to 92,000 psi.

As defined herein, thickness is a dimension extending from a first surface of the composite film 102 to a second surface of the composite film 102 in the z-direction. In some embodiments, the composite film 102 has a thickness from 0.01 mm to 0.1 mm. In other embodiments, the composite film 102 has a thickness from 0.01 mm to 0.09 mm. In other embodiments, the composite film 102 has a thickness from 0.01 mm to 0.085 mm. In other embodiments, the composite film 102 has a thickness from 0.01 mm to 0.075 mm. In other embodiments, the composite film 102 has a thickness from 0.01 mm to 0.065 mm. In other embodiments, the composite film 102 has a thickness from 0.01 mm to 0.059 mm. In other embodiments, the composite film 102 has a thickness from 0.01 mm to 0.05 mm. In other embodiments, the composite film 102 has a thickness from 0.01 mm to 0.04 mm. In other embodiments, the composite film 102 has a thickness from 0.01 mm to 0.03 mm. In other embodiments, the composite film 102 has a thickness from 0.01 mm to 0.025 mm. In other embodiments, the composite film 102 has a thickness from 0.01 mm to 0.015 mm.

In some embodiments, the composite film 102 has a thickness from 0.015 mm to 0.1 mm. In other embodiments, the composite film 102 has a thickness from 0.025 mm to 0.1 mm. In other embodiments, the composite film 102 has a thickness from 0.03 mm to 0.1 mm. In other embodiments, the composite film 102 has a thickness from 0.045 mm to 0.1 mm. In other embodiments, the composite film 102 has a thickness from 0.05 mm to 0.1 mm. In other embodiments, the composite film 102 has a thickness from 0.059 mm to 0.1 mm. In other embodiments, the composite film 102 has a thickness from 0.065 mm to 0.1 mm. In other embodiments, the composite film 102 has a thickness from 0.075 mm to 0.1 mm. In other embodiments, the composite film 102 has a thickness from 0.09 mm to 0.1 mm. In other embodiments, the composite film 102 has a thickness from 0.095 mm to 0.1 mm.

In some embodiments, the composite film 102 has a thickness from 0.02 mm to 0.045 mm. In other embodiments, the composite film 102 has a thickness from 0.025 mm to 0.035 mm. In other embodiments, the composite film 102 has a thickness from 0.03 mm to 0.04 mm. In other embodiments, the composite film 102 has a thickness from 0.02 mm to 0.025 mm. In other embodiments, the composite film 102 has a thickness from 0.075 mm to 0.095 mm. In other embodiments, the composite film 102 has a thickness from 0.065 mm to 0.08 mm. In other embodiments, the composite film 102 has a thickness from 0.059 mm to 0.098 mm.

In some embodiments, the composite film 102 has a clarity that allows the cell culture 116 to be viewed in the cell culture compartment 114, through the composite film 102. As used herein, clarity is quantified as the total transmittance (%) through the composite film 102. Specifically, a higher total transmittance indicates a higher degree of clarity whereas a lower total transmittance indicates a lower degree of clarity. In some embodiments, the composite film 102 has a total transmittance from 70% to 100%. In other embodiments, the composite film 102 has a total transmittance from 75% to 100%. In other embodiments, the composite film 102 has a total transmittance from 80% to 100%. In other embodiments, the composite film 102 has a total transmittance from 85% to 100%. In other embodiments, the composite film 102 has a total transmittance from 90% to 100%. In other embodiments, the composite film 102 has a total transmittance from 95% to 100%.

In some embodiments, the composite film 102 has a total transmittance from 70% to 95%. In other embodiments, the composite film 102 has a total transmittance from 70% to 90%. In other embodiments, the composite film 102 has a total transmittance from 70% to 85%. In other embodiments, the composite film 102 has a total transmittance from 70% to 80%. In other embodiments, the composite film 102 has a total transmittance from 70% to 85%.

In some embodiments, the composite film 102 has a total transmittance from 75% to 85%. In other embodiments, the composite film 102 has a total transmittance from 90% to 95%. In other embodiments, the composite film 102 has a total transmittance from 80% to 95%. In other embodiments, the composite film has a total transmittance from 75% to 95%. In other embodiments, the composite film has a total transmittance from 80% to 90%. In other embodiments, the composite film has a total transmittance from 75% to 90%.

In some embodiments, the reduced thickness of the composite film 102 results in a cell culture bag 100 with non-polar gas permeation, thereby allowing oxygen to flow to the cells to promote cellular survival and growth. As defined herein, non-polar gas permeation is an $O_2$ flux of at least 2,000 $cm^3/m^2/atm/day$. For purposes of this definition, water vapor is not a non-polar gas.

$O_2$ flux is defined herein as the amount of oxygen that is deliverable to the cell culture 116 through the composite film 102. In some embodiments, the composite film 102 has an $O_2$ flux from 2,000 $cm^3/m^2/atm/day$ to 20,000 $cm^3/m^2/atm/day$. In some embodiments, the composite film 102 has an $O_2$ flux from 5,000 $cm^3/m^2/atm/day$ to 20,000 $cm^3/m^2/atm/day$. In other embodiments, the composite film 102 has an $O_2$ flux from 10,000 $cm^3/m^2/atm/day$ to 20,000 $cm^3/m^2/atm/day$. In other embodiments, the composite film 102 has an $O_2$ flux from 15,000 $cm^3/m^2/atm/day$ to 20,000 $cm^3/m^2/atm/day$.

In some embodiments, the composite film 102 has an $O_2$ flux from 2,000 $cm^3/m^2/atm/day$ to 15,000 $cm^3/m^2/atm/day$. In other embodiments, the composite film 102 has an $O_2$ flux from 2,000 $cm^3/m^2/atm/day$ to 10,000 $cm^3/m^2/atm/day$. In other embodiments, the composite film 102 has an $O_2$ flux from 2,000 $cm^3/m^2/atm/day$ to 7,500 $cm^3/m^2/atm/day$. In other embodiments, the composite film 102 has an $O_2$ flux from 2,000 $cm^3/m^2/atm/day$ to 5,000 $cm^3/m^2/atm/day$. In other embodiments, the composite film 102 has an $O_2$ flux from 2,000 $cm^3/m^2/atm/day$ to 2,500 $cm^3/m^2/atm/day$.

In some embodiments, the composite film 102 has an $O_2$ flux from 3,000 $cm^3/m^2/atm/day$ to 8,000 $cm^3/m^2/atm/day$. In other embodiments, the composite film 102 has an $O_2$ flux from 6,000 $cm^3/m^2/atm/day$ to 16,000 $cm^3/m^2/atm/day$. In other embodiments, the composite film 102 has an $O_2$ flux from 4,500 $cm^3/m^2/atm/day$ to 5,000 $cm^3/m^2/atm/day$. In other embodiments, the composite film 102 has an $O_2$ flux from 15,000 $cm^3/m^2/atm/day$ to 17,500 $cm^3/m^2/atm/day$. In other embodiments, the composite film 102 has an $O_2$ flux from 12,000 $cm^3/m^2/atm/day$ to 18,000 $cm^3/m^2/atm/day$. In other embodiments, the composite film 102 has an $O_2$ flux from 17,500 $cm^3/m^2/atm/day$ to 19,000 $cm^3/m^2/atm/day$.

As described herein, the impregnation of the second material into the first material creates a durable bond between the first and second materials of the composite film 102. In some embodiments, the durable bond between the first and second materials is sufficient to provide the composite film 102 a peel strength from 0.25 N/mm to 10 N/mm. As defined herein, a peel strength of the composite film 102 is the measure of the average force to part (i.e., separate) the composite film 102 from a second film (or second material) to which the composite film 102 is bonded. As defined herein, the peel strength may be the strength required to separate the ePTFE of the composite film 102 and FEP of the second film or the strength required to separate the FEP of the composite film 102 and the FEP of the second film. In some embodiments, the peel strength required to separate the ePTFE of the composite film 102 and the FEP of the second film is from 0.25 N/mm to 10 N/mm. In other embodiments, the peel strength required to separate the ePTFE of the composite film 102 and the FEP of the second film is from 0.5 N/mm to 10 N/mm. In other embodiments, the peel strength required to separate the ePTFE of the composite film 102 and the FEP of the second film is from 1.0 N/mm to 10 N/mm. In other embodiments, the peel strength required to separate the ePTFE of the composite film 102 and the FEP of the second film is from 2.5 N/mm to 10 N/mm. In other embodiments, the peel strength required to separate the ePTFE of the composite film 102 and the FEP of the second film is from 5 N/mm to 10 N/mm. In other embodiments, the peel strength required to separate the ePTFE of the composite film 102 and the FEP of the second film is from 7.5 N/mm to 10 N/mm.

In some embodiments, the peel strength required to separate the ePTFE of the composite film 102 and the FEP of the second film is from 0.25 N/mm to 7.5 N/mm. In other embodiments, the peel strength required to separate the ePTFE of the composite film 102 and the FEP of the second film is from 0.25 N/mm to 5 N/mm. In other embodiments, the peel strength required to separate the ePTFE of the composite film 102 and the FEP of the second film is from 0.25 N/mm to 2.5 N/mm. In other embodiments, the peel strength required to separate the ePTFE of the composite film 102 and the FEP of the second film is from 0.25 N/mm to 1.0 N/mm. In other embodiments, the peel strength required to separate the ePTFE of the composite film 102 and the FEP of the second film is from 0.25 N/mm to 0.5 N/mm.

In some embodiments, the peel strength required to separate the ePTFE of the composite film 102 and the FEP of the second film is from 0.5 N/mm to 7.5 N/mm. In other embodiments, the peel strength required to separate the ePTFE of the composite film 102 and the FEP of the second film is from 1.0 N/mm to 5 N/mm. In other embodiments, the peel strength required to separate the ePTFE of the composite film 102 and the FEP of the second film is from 2.5 N/mm to 7.5 N/mm. In other embodiments, the peel strength required to separate the ePTFE of the composite film 102 and the FEP of the second film is from 1.0 N/mm to 2.5 N/mm. In other embodiments, the peel strength required to separate the ePTFE of the composite film 102 and the FEP of the second film is from 5 N/mm to 7.5 N/mm.

In some embodiments, the peel strength required to separate the FEP of the composite film 102 and the FEP of the second film is from 0.25 N/mm to 10 N/mm. In other embodiments, the peel strength required to separate the FEP of the composite film 102 and the FEP of the second film is from 0.5 N/mm to 10 N/mm. In other embodiments, the peel strength required to separate the FEP of the composite film 102 and the FEP of the second film is from 1.0 N/mm to 10 N/mm. In other embodiments, the peel strength required to separate the FEP of the composite film 102 and the FEP of the second film is from 2.5 N/mm to 10 N/mm. In other embodiments, the peel strength required to separate the FEP of the composite film 102 and the FEP of the second film is from 5 N/mm to 10 N/mm. In other embodiments, the peel strength required to separate the FEP of the composite film 102 and the FEP of the second film is from 7.5 N/mm to 10 N/mm.

In some embodiments, the peel strength of the FEP required to separate the composite film 102 and the FEP of the second film is from 0.25 N/mm to 7.5 N/mm. In other embodiments, the peel strength required to separate the FEP of the composite film 102 and the FEP of the second film is from 0.25 N/mm to 5 N/mm. In other embodiments, the peel strength required to separate the FEP of the composite film 102 and the FEP of the second film is from 0.25 N/mm to 2.5 N/mm. In other embodiments, the peel strength required to separate the FEP of the composite film 102 and the FEP of the second film is from 0.25 N/mm to 1.0 N/mm. In other embodiments, the peel strength required to separate the FEP of the composite film 102 and the FEP of the second film is from 0.25 N/mm to 0.5 N/mm.

In some embodiments, the peel strength required to separate the FEP of the composite film 102 and the FEP of the second film is from 0.5 N/mm to 7.5 N/mm. In other embodiments, the peel strength required to separate the FEP of the composite film 102 and the FEP of the second film is from 1.0 N/mm to 5 N/mm. In other embodiments, the peel strength required to separate the FEP of the composite film 102 and the FEP of the second film is from 2.5 N/mm to 7.5 N/mm. In other embodiments, the peel strength required to separate the FEP of the composite film 102 and the FEP of the second film is from 1.0 N/mm to 2.5 N/mm. In other embodiments, the peel strength required to separate the FEP of the composite film 102 and the FEP of the second film is from 5 N/mm to 7.5 N/mm.

In the embodiments depicted in FIGS. 1 and 2, the cell culture bag 100 is made by wrapping a composite film 102 around a heating element to form a tube. In some embodiments, a first end of the composite film 102 overlaps a second end of the composite film 102 and heat and pressure are used to bond the composite film 102 to itself and create a composite film tube 104 with a longitudinal lap seam 118. The composite film tube 104 is then flattened in a direction perpendicular to a longitudinal axis L of the composite film tube 104.

A second piece of composite film 130 is then folded over on itself. A first end 106 of the composite film tube 104 is placed between the two layers of folded composite film 130. Heat and pressure are used to bond the folded composite film 130 to the composite film tube 104 to create a lap seam 132 closing off the first end 106 of the composite film tube 104. The folded composite film 130 bonds to itself outside of the composite film tube 104 in a fin seam 142. A third piece of composite film 140 is then folded over on itself. A second end 108 of the composite film tube 104 is placed between the two layers of folded composite film 140. A non-adhering element (not illustrated) is placed within the cell culture bag 100 extending into the folded composite film 140 to create an area that will not be bonded. Heat and pressure are used to bond the folded composite film 140 to the composite film tube 104 to create a lap seam 144 closing off the second end of the composite film tube 104. The folded composite film 140 bonds to itself outside of the composite film tube 104 in a fin seam 146. A slit is cut into the fin seam 146 of the cell culture bag 100. The non-adhering element is removed. A port adapter 110 is placed in the area that is not bonded. The port adapter 110 may be used in conjunction with various ports (not shown), depending on the desired end use application. For example, in one embodiment, a non-collapsible port assembly may be used. Heat and pressure may be used to bond the port adapter 110 to the folded composite film 140, creating the fin seam (not shown) and forming the cell culture bag 100.

In yet other embodiments, the cell culture bag 100 is made generally in accordance with the teachings provided in P.C.T. Patent Application No. WO 2019/209268 to Alford et al., which is incorporated by reference herein.

In other embodiments, other configurations of the cell culture bag 100 may be used. For example, in some embodiments, the cell culture bag 100 may be configured generally in accordance with the teachings of U.S. Patent Application Publication No. 2016/0030283 A1 to Snyder et al.

In an alternate embodiment, two composite films 102 may be used, one composite film 102 on each side of the composite film tube 104.

The volume within the cell culture bag 100 may be varied depending on the application. For example, the cell culture bag 100, in an embodiment, has a volume from 1 mL to 200 L. In other embodiments, the cell culture bag 100 has a volume from 100 mL to 200 L. In other embodiments, the cell culture bag 100 has a volume from 500 mL to 200 L. In other embodiments, the cell culture bag 100 has a volume from 1 L to 200 L. In other embodiments, the cell culture bag 100 has a volume from 5 L to 200 L. In other embodiments, the cell culture bag 100 has a volume from 10 L to 200 L. In other embodiments, the cell culture bag 100 has a volume from 50 L to 200 L. In other embodiments, the cell culture bag 100 has a volume from 100 L to 200 L.

In some embodiments, the cell culture bag 100 has a volume from 1 mL to 100 L. In other embodiments, the cell culture bag 100 has a volume from 1 mL to 50 L. In other embodiments, the cell culture bag 100 has a volume from 1 mL to 10 L. In other embodiments, the cell culture bag 100 has a volume from 1 mL to 5 L. In other embodiments, the cell culture bag 100 has a volume from 1 mL to 2 L. In other embodiments, the cell culture bag 100 has a volume from 1 mL to 1 L. In other embodiments, the cell culture bag 100 has a volume from 1 mL to 500 mL. In other embodiments, the cell culture bag 100 has a volume from 1 mL to 250 mL. In other embodiments, the cell culture bag 100 has a volume from 1 mL to 100 mL. In other embodiments, the cell culture bag 100 has a volume from 1 mL to 20 mL.

In some embodiments, the cell culture bag 100 has a volume from 1 mL to 150 L. In other embodiments, the cell culture bag 100 has a volume from 100 mL to 50 L. In other embodiments, the cell culture bag 100 has a volume from 500 mL to 1 L. In other embodiments, the cell culture bag 100 has a volume from 10 mL to 10 L. In other embodiments, the cell culture bag 100 has a volume from 5 L to 20 L. In other embodiments, the cell culture bag 100 has a volume from 1 L to 50 L.

In some embodiments, the cell culture bag 100 is used for cell and gene therapies related to many conditions including various cancers, neurological diseases, infectious diseases such as tuberculosis and cystic fibrosis, ulcerative colitis, peripheral artery disease, aneurysm, heart disease, Alzheimer's and Parkinson's diseases, autism, ophthalmology conditions, diabetes, and other pathologies. In some embodiments, the cell culture bag 100 is used for the in vitro culturing of cells in the activation, transfection, expansion and proliferation stages.

Figure 3:
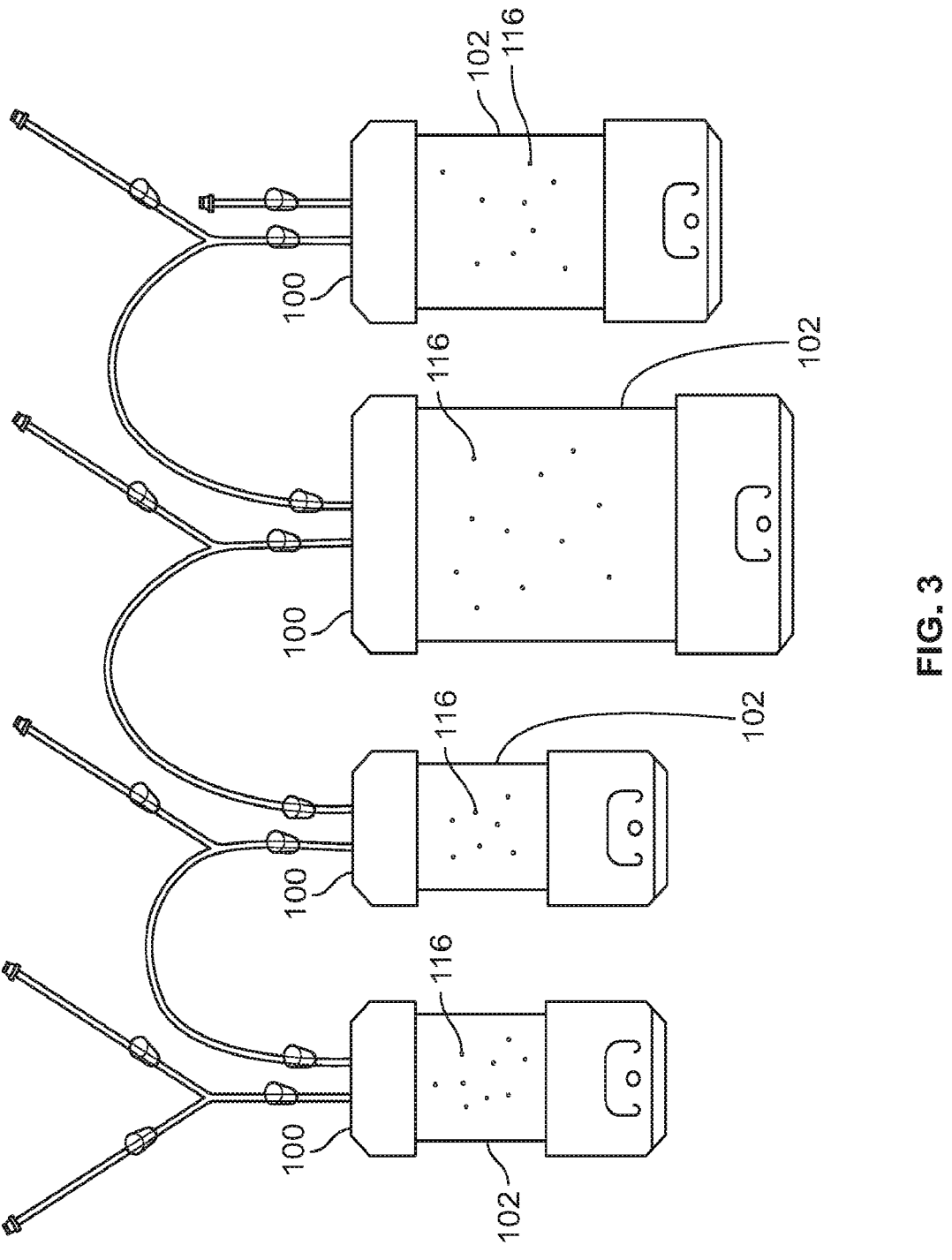
FIG. 3 is a perspective view of four cell culture bags linked in series, in accordance with some embodiments herein.

In some embodiments, at least two cell culture bags 100 are linked together in series, in fluid communication, to allow for aseptic transfer of the cell culture 116 during the cell culturing process, as depicted in FIG. 3. In some embodiments, three cell culture bags are linked in series. In other embodiments, four cell culture bags are linked in series, depicted in FIG. 3. In other embodiments, five or more cell culture bags 100 may be linked in series. In some embodiments, cell culture bags 100 within the series have different characteristics based on the requirements of the cell culture 116. For example, the size and $O_2$ flux of each cell culture bag 100 may be tailored based on the stage of the cell culturing process. In some embodiments, two cell culture bags 100 with different sizes and differing $O_2$ flux may be linked together. In other embodiments, three cell culture bags 100 with different sizes and differing $O_2$ flux may be linked together. As one example, during stages in which cell culture growth is required, the $O_2$ flux of the composite film 102 may be increased compared to the $O_2$ flux in other cell culture bags 100. In other embodiments, a cell culture bag 100 may be connected to a freeze container bag such as, for example, the Gore® STA-PURE™ Flexible Freeze Container, for aseptic transferal of the cell culture 116 for long term storage of anywhere from two months to over 20 years.

In some embodiments, an inner or an outer surface of the cell culture bag 100 is hydrophobic or includes a hydrophobic coating. In other embodiments, an inner or an outer surface of the cell culture bag 100 is hydrophilic or includes a hydrophilic coating.

A variety of cell types may be grown in the cell culture bags 100 including, but not limited to, T cells, TCR cells, connective tissue cells, skeletal cells, cardiac cells, epithelial cells, neural cells, endocrine cells, immune cells, lymphocytes, and melanocytes. Similarly, a variety of growth media is available in which the cell types may grow, depending on the particular growth requirements of the cells and the growth conditions. In some embodiments, a suitable growth media includes, for example, a nutrient or lysogeny broth with added hormones and/or growth factors.

In some embodiments, a coating or treatment is applied to the inner surface of the cell culture bag compartment 114 of the cell culture bag 100 to achieve a desired purpose. For example, the cell culture bag 100 may include a coating or treatment on an inner surface of the cell culture compartment 114 to promote cell growth and metabolism. In other embodiments, the coating or treatment may promote cell activation, transfection, expansion and/or proliferation. However, any functional coating or treatment that is applied to the cell culture bag compartment 114 is one that does not hinder the $O_2$ flux of the composite film 102. For example, in some embodiments, the coating or treatment is applied to the cell culture bag 100 in a pattern or only over a portion of the inner surface of the cell culture compartment 114. In other embodiments, the composite film 102 is formed with an $O_2$ flux above a threshold level such that when the surface of the composite film 102 is treated, the resultant composite film 102 has an $O_2$ flux of at least 2,000 $cm^3/m^2/atm/day$. In other embodiments, the composite film 102 is formed with an $O_2$ flux, thickness and tensile strength that allows the cell culture bag 100 to be functionalized post-production but prior to use. In some embodiments, the composite film 102 is formed with a surface area and/or surface energy that allows the cell culture bag 100 to be functionalized post-production but prior to use.

Figure 4:
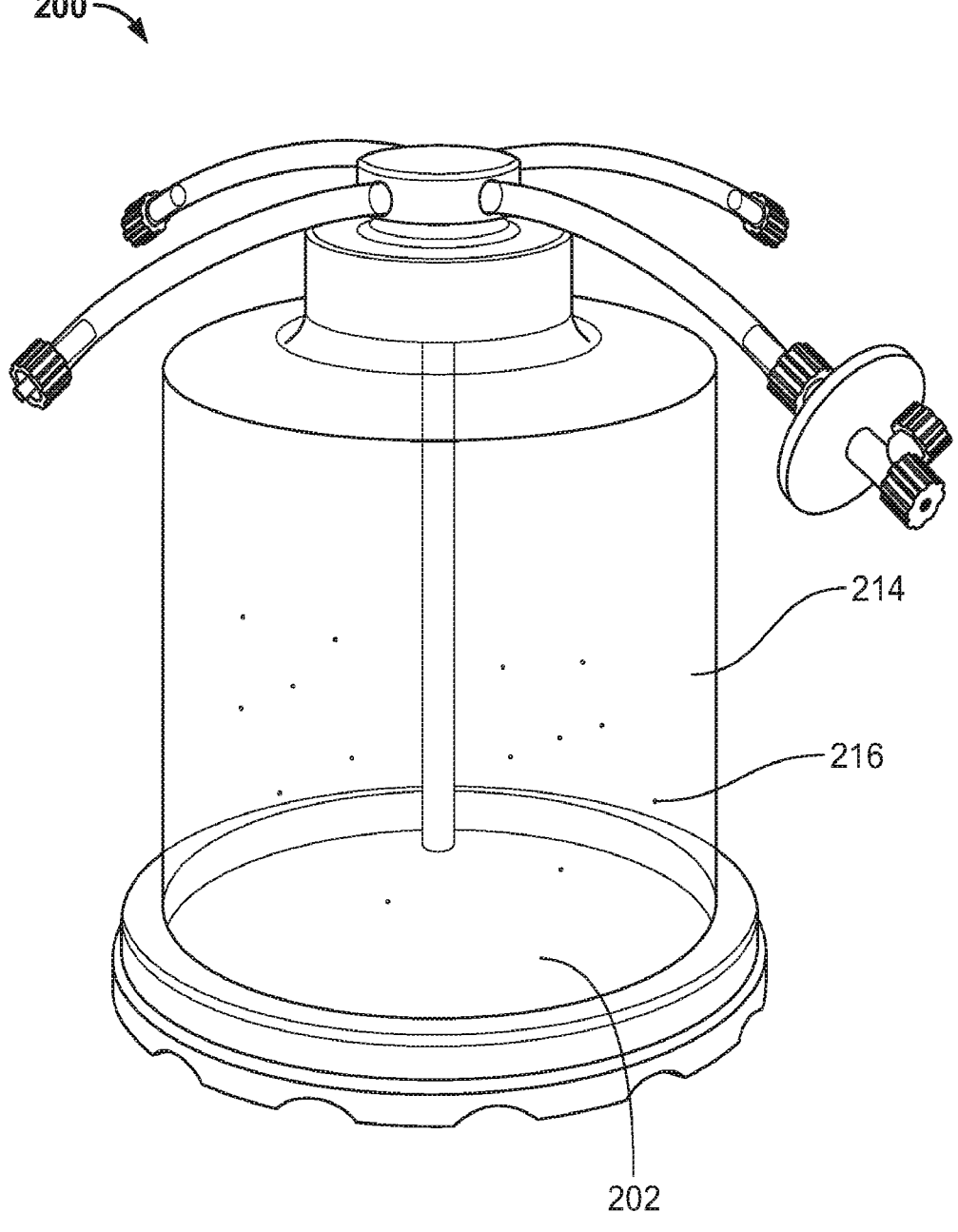
FIG. 4 is a front view of a cell culture container in accordance with some embodiments herein.

FIG. 4 depicts a cell culture container 200 according to some embodiments of the present disclosure. The cell culture container 200 includes a cell culture compartment 214 configured to receive a cell culture 216. The cell culture container 200 also includes a composite film 202 positioned at, or connected to, the bottom of the cell culture container 200, in contact with the cell culture 216 contained therein. The composite film 202 may be substantially the same or the same as the composite film 102 with all of the characteristics of the composite film 102 described herein. In some embodiments, the composite film 202 is a fluoropolymer composite film which provides the durability (e.g., tensile strength and puncture resistance) as well as $O_2$ flux and surface area required to support cell growth. In addition, in some embodiments, the fluoropolymer composite film 202 reduces the amount of leachables and extractables.

The volume within the cell culture compartment 214 of the cell culture container 200 may be varied depending on the desired application. For example, the cell culture container 200, in an embodiment, has a volume from 1 mL to 200 L. In other embodiments, the cell culture container 200 has a volume from 100 mL to 200 L. In other embodiments, the cell culture container 200 has a volume from 500 mL to 200 L. In other embodiments, the cell culture container 200 has a volume from 1 L to 200 L. In other embodiments, the cell culture container 200 has a volume from 10 L to 200 L. In other embodiments, the cell culture container 200 has a volume from 50 L to 200 L. In other embodiments, the cell culture container 200 has a volume from 100 L to 200 L.

In some embodiments, the cell culture container 200 has a volume from 1 mL to 100 L. In other embodiments, the cell culture container 200 has a volume from 1 mL to 50 L. In other embodiments, the cell culture container 200 has a volume from 1 mL to 10 L. In other embodiments, the cell culture container 200 has a volume from 1 mL to 1 L. In other embodiments, the cell culture container 200 has a volume from 1 mL to 750 mL. In other embodiments, the cell culture container 200 has a volume from 1 mL to 500 mL. In other embodiments, the cell culture container 200 has a volume from 1 mL to 100 mL. In other embodiments, the cell culture container 200 has a volume from 1 mL to 20 mL.

In some embodiments, the cell culture container 200 has a volume from 1 mL to 150 L. In other embodiments, the cell culture container 200 has a volume from 100 mL to 20 L. In other embodiments, the cell culture container 200 has a volume from 500 mL to 1 L. In other embodiments, the cell culture container 200 has a volume from 1 L to 2 L. In other embodiments, the cell culture container 200 has a volume from 2 L to 100 L. In other embodiments, the cell culture container 200 has a volume from 250 mL to 750 mL.

In some embodiments, varying the volume of the cell culture container 200 results in corresponding changes to the surface area of the composite film 202 such that the surface area to volume ratio (SA/V) remains constant or close to constant as the volume of the container changes to ensure proper gas exchange for the cell contained therein.

In some embodiments, the cell culture container 200 is used for cell and gene therapies related to many conditions including, but not limited to, various cancers, neurological diseases, infectious diseases such as tuberculosis and cystic fibrosis, ulcerative colitis, peripheral artery disease, aneurysm, heart disease, Alzheimer's and Parkinson's diseases, autism, ophthalmology conditions, diabetes, and other pathologies. In some embodiments, the cell culture container 200 is used for the in vitro culturing of cells in the activation, transfection, expansion and proliferation stages.

Test Methods

O₂ Flux

O$_2$ flux of the composite films described herein was measured according to ASTM D1434-82 (2015).

Tensile Strength

Tensile strength of the composite films described herein was measured according to ASTM D412-16 Die F.

Total Organic Carbon in Water

TOC of the composite films described herein was measured according to US Pharmacopeia (USP) 643 and with equipment that utilizes a high temperature wet oxidation reaction of UV-promoted chemical oxidation (*Ultra-Clean Technology Handbook: Volume* 1: *Ultra-Pure Water*, Ohmi, Tadahiro; CRC Press, 1993, pp. 497-517). Purified water was placed in contact with the composite film for 24 hours at 70° C., for example at a ratio of 3 cm$^2$ of article surface area to 1 mL of water. The water was removed from contact with the polymer and tested in a TOC analyzer. A suitable The composite film was made generally in accordance with U.S. Pat. No. 7,521,010 to Kennedy.

The composite film had a FEP penetration thickness of 0.35 μm and an unpenetrated ePTFE thickness of 14.86 μm.

The composite film was tested for O$_2$ flux using the test methods set forth in ASTM D1434. The composite film was determined to have an O$_2$ flux of 7,786 cm$^3$/m$^2$/atm/day.

The composite film was also tested for tensile strength in at least one direction using the test methods set forth in ASTM 412 Die F. The composite film was determined to have a minimal tensile strength of 24,100 psi in a machine direction and a transverse direction.

The composite had a peel strength of 0.43 N/mm for the FEP/ePTFE interface and a peel strength of 1.60 N/mm for the FEP/FEP interface.

The total transmittance of the composite film was determined to be 93.4%.

The results of Examples 1 and 1 are found in Table 1.

TABLE 1

| Film | Composition | Thickness (μm) | FEP Penetration (μm) | Unpenetrated ePTFE (μm) | Tensile Strength (psi) | O₂ Flux (cm³/m²/atm/ day) | Total Transmittance (%) | Peel FEP to PTFE (N/mm) | Peel FEP to FEP (N/mm) |
|---|---|---|---|---|---|---|---|---|---|
| 1 | 70% ePTFE, 30% FEP | 27.14 | 0.45 | 19.89 | 10,520 | 11,500 | 91.0 | 0.42 | 1.12 |
| 2 | 78% ePTFE, 22% FEP | 19.78 | 0.35 | 14.86 | 24,100 | 7,786 | 93.4 | 0.43 | 1.60 | piece of equipment is a Sievers M9 TOC analyzer from SUEZ WATER TECHNOLOGIES & SOLUTIONS.

Peel Strength

Peel strength of composite films described herein was measured according to ASTM F88-15.

Total Transmittance

Average total transmittance of 380 to 740 nm wavelengths through composite films described herein was measured according to ASTM D1003-13.

EXAMPLE 1

A composite film with a thickness of 27.14 μm was obtained that contained 70 wt % ePTFE and 30 wt % FEP. The composite film was made generally in accordance with U.S. Pat. No. 7,521,010 to Kennedy.

The composite film had a FEP penetration thickness of 0.45 μm and an unpenetrated ePTFE thickness of 19.89 μm.

The composite film was tested for O$_2$ flux using the test methods set forth in ASTM D1434. The composite was determined to have an O$_2$ flux of 11,500 cm$^3$/m$^2$/atm/day.

The composite film was also tested for tensile strength in at least one direction using the test methods set forth in ASTM 412 Die F. The composite film was determined to have a minimum tensile strength of 10,520 psi in a machine direction and a transverse direction.

The composite film displayed a peel strength of 0.42 N/mm for the FEP/ePTFE interface and a peel strength of 1.12 N/mm for the FEP/FEP interface.

The total transmittance of the composite film was determined to be 91.0%.

EXAMPLE 2

A composite film with a thickness of 19.78 μm that contained 78 wt % ePTFE and 22 wt % FEP was obtained.

In comparison, conventional composite films have been formed by bonding FEP to skived ePTFE. When tested, these composite films are expected to have an FEP penetration, peel strength, tensile strength (machine and transverse direction) and an O$_2$ flux that falls outside of the ranges provided in the Examples and description described herein.

Further, conventional composite films formed by bonding FEP to ePTFE have been made. When tested, these conventional composite films are expected to have a total transmittance that falls outside of the ranges provided in the Examples and description described herein.

What is claimed is:

1. A cell culture bag comprising:
a body formed of a composite film comprising a first fluoropolymer and a second fluoropolymer,
wherein the body defines a cell culture compartment configured to hold a cell culture,
wherein the first fluoropolymer has a first thickness,
wherein the second fluoropolymer at least partially impregnates the first thickness of the first fluoropolymer,
wherein the composite film has a second thickness from 0.01 mm to 0.059 mm,
wherein the composite film has a tensile strength in one direction from 10,000 psi to 92,000 psi,
wherein the composite film has an O$_2$ flux from 2,000 cm$^3$/m$^2$/atm/day to 20,000 cm$^3$/m$^2$/atm/day, and
wherein the composite film has a total transmittance from 70% to 100%, as measured according to ASTM D1003-13.

2. The cell culture bag of claim 1, wherein the composite film does not comprise silicone.

3. The cell culture bag of claim 1, wherein the second fluoropolymer impregnates from 0.00001 mm to 0.02 mm of the first thickness of the first fluoropolymer.

4. The cell culture bag of claim 1, wherein the composite film has a total thickness from 0.02 mm to 0.059 mm.

5. The cell culture bag of claim 1, wherein the composite film has a total organic carbon (TOC) in water of 0.00001 mg/cm$^2$ to 1 mg/cm$^2$.

6. The cell culture bag of claim 1, wherein a peel strength of the composite film is 0.25 N/mm to 10 N/mm.

7. The cell culture bag of claim 1, wherein the first fluoropolymer is expanded polytetrafluoroethylene and the second fluoropolymer is fluorinated ethylene propylene.

8. The cell culture bag of claim 1, wherein the first fluoropolymer is densified expanded polytetrafluoroethylene and the second fluoropolymer is fluorinated ethylene-propylene.

9. A cell culture bag comprising:
a tube extending from a first end to a second end and defining a cell culture compartment,
wherein the tube is formed of a first composite film comprising a first fluoropolymer and a second fluoropolymer,
wherein the first fluoropolymer has a first thickness,
wherein the second fluoropolymer at least partially impregnates the first thickness of the first fluoropolymer,
wherein the first composite film has a second thickness of 0.01 mm to 0.059 mm,
wherein the first composite film has an O$_2$ flux of 2,000 cm$^3$/m$^2$/atm/day to 20,000 cm$^3$/m$^2$/atm/day,
wherein the first composite film has a tensile strength of 10,000 psi to 92,000 psi, and
wherein the first composite film has a total transmittance of at least 70%, as measured according to ASTM D1003-13;
a first joint at a first end;
a second composite film configured to be folded over the first joint to form a first lap seam over the first joint; and
a second lap seam extending longitudinally from the first end to the second end,
wherein the second lap seam is formed by overlapping edges of the first composite film.

10. The cell culture bag of claim 9, further comprising:
a second joint at a second end; and
a third composite film configured to be folded over the second joint to form a third lap seam.

11. The cell culture bag of claim 9, wherein the second fluoropolymer impregnates 0.00001 mm to 0.005 mm of the first thickness of the first fluoropolymer.

12. The cell culture bag of claim 9, wherein the first composite film has a thickness of 0.02 mm to 0.059 mm.

13. The cell culture bag of claim 9, wherein the first composite film has a total organic carbon (TOC) of less than 1 mg/cm$^2$.

14. The cell culture bag of claim 9, wherein the first fluoropolymer is expanded polytetrafluoroethylene and the second fluoropolymer is fluorinated ethylene propylene.

15. The cell culture bag of claim 9, wherein the first fluoropolymer is densified expanded polytetrafluoroethylene and the second fluoropolymer is fluorinated ethylene-propylene.

16. The cell culture bag of claim 9, further comprising at least one access port in fluid communication with the cell culture compartment.

17. The cell culture bag of claim 9, wherein a peel strength of the first composite film is 0.25 N/mm to 10 N/mm.

18. A cell culture assembly, comprising:
a plurality of cell culture bags connected in series, each of the plurality of cell culture bags comprising:
a body formed of a composite film comprising a first fluoropolymer and a second fluoropolymer,
wherein the body defines a cell culture compartment configured to hold a cell culture,
wherein the first fluoropolymer has a first thickness,
wherein the second fluoropolymer at least partially impregnates the first thickness of the first fluoropolymer,
wherein the composite film has a second thickness from 0.01 mm to 0.059 mm,
wherein the composite film has a tensile strength in one direction from 10,000 psi to 92,000 psi,
wherein the composite film has an O$_2$ flux from 2,000 cm$^3$/m$^2$/atm/day to 20,000 cm$^3$/m$^2$/atm/day, and
wherein a total transmittance of the composite film is from 70% to 100%, as measured according to ASTM D1003-13.

19. The cell culture assembly of claim 18, wherein a first cell culture bag of the plurality of cell culture bags has a first O$_2$ flux and a second cell culture bag of the plurality of cell culture bags has a second O$_2$ flux, and
wherein the first O$_2$ flux and the second O$_2$ flux are different.

20. The cell culture assembly of claim 18, wherein a first cell culture bag of the plurality of cell culture bags has a first volume and a second cell culture bag of the plurality of cell culture bags has a second volume, and
wherein the first volume is different than the second volume.

* * * * *